(12) United States Patent
Yamada et al.

(10) Patent No.: US 7,488,420 B2
(45) Date of Patent: Feb. 10, 2009

(54) CHROMATOGRAPHIC SEPARATOR (75) Inventors: Kyosuke Yamada, Tokyo (JP); Naoko Suzuki, Tokyo (JP); Takayuki Masuda, Tokyo (JP)

(73) Assignee: Organo Corporation, Koto-ku (JP)

( * ) Notice: Subject to any disclaimer, the term of this patent is extended or adjusted under 35 U.S.C. 154(b) by 0 days.

(21) Appl. No.: 11/547,478

(22) PCT Filed: Mar. 16, 2005

(86) PCT No.: PCT/JP2005/004612

§ 371 (c)(1),
(2), (4) Date: Oct. 2, 2006

(87) PCT Pub. No.: WO2005/097286

PCT Pub. Date: Oct. 20, 2005

(65) Prior Publication Data
US 2007/0199873 A1 Aug. 30, 2007

(30) Foreign Application Priority Data

Apr. 5, 2004 (JP) .............................. 2004-111074

(51) Int. Cl.
*B01D 15/08* (2006.01)
(52) U.S. Cl. ..................................... 210/198.2; 210/659
(58) Field of Classification Search .............. 210/198.2, 210/635, 656, 659, 264, 269
See application file for complete search history.

(56) References Cited

U.S. PATENT DOCUMENTS

| 4,267,054 | A | | 5/1981 | Yoritomi et al. | |
|---|---|---|---|---|---|
| 4,379,751 | A | | 4/1983 | Yoritomi et al. | |
| 4,970,002 | A | * | 11/1990 | Ando et al. | 210/659 |
| 5,456,825 | A | * | 10/1995 | Negawa et al. | 210/98 |
| 5,635,072 | A | * | 6/1997 | Moran | 210/659 |
| 5,667,693 | A | * | 9/1997 | Hester et al. | 210/635 |
| 6,328,895 | B1 | * | 12/2001 | Masuda et al. | 210/659 |
| 6,331,250 | B1 | * | 12/2001 | Kaneko et al. | 210/635 |
| 6,409,922 | B1 | * | 6/2002 | Kaneko et al. | 210/659 |
| 6,482,323 | B2 | * | 11/2002 | Tanimura et al. | 210/635 |
| 6,488,858 | B2 | * | 12/2002 | Tanimura et al. | 210/659 |
| 6,685,781 | B2 | * | 2/2004 | Hyoky et al. | 127/46.1 |
| 2001/0030158 | A1 | * | 10/2001 | Tanimura et al. | 210/656 |
| 2002/0088754 | A1 | * | 7/2002 | Tanimura et al. | 210/656 |

FOREIGN PATENT DOCUMENTS

| EP | 1003036 A | 5/2000 |
|---|---|---|
| JP | 6-39205 A | 2/1994 |
| JP | 7-328305 A | 12/1995 |
| JP | 2962589 B | 8/1999 |
| JP | 2001-334103 A | 12/2001 |
| JP | 2001-354690 A | 12/2001 |

OTHER PUBLICATIONS

Mata, V. et al., "Separation of Ternary Mixtures by Pseudo-Simulated Moving Bed Chromatography", Journal of Chromatography A, 2001, pp. 23-40, No. 939, Elsevier Science B.V.

* cited by examiner

*Primary Examiner*—Ernest G Therkorn
(74) *Attorney, Agent, or Firm*—Smith Patent Office

(57) ABSTRACT

A chromatographic separator characterized in that two pumps are employed for controlling chromatographic separation that combines a first process for supplying at least one of feed solution and eluent into a circulation system and extracting the same quantity as that of liquid supplied into the circulation system from one position of a packed column where some component is enriched in the circulation system, and a second process for circulating liquid in the system without supplying the feed solution and eluent and extracting the separated component at all. Easy-to-control chromatographic separator, in which a total number of pumps to be used is decreased and high separation performance is attained through a simple structure, can thereby be provided.

2 Claims, 3 Drawing Sheets

CHROMATOGRAPHIC SEPARATOR

REFERENCE TO RELATED APPLICATIONS

This application is a 371 of PCT/JP05/04612 filed Mar. 16, 2005.

TECHNICAL FIELD OF THE INVENTION

The present invention relates to a chromatographic separator which performs a simulated moving-bed type chromatographic separation by connecting a plurality of unit packed columns in series at an endless form, each unit packed column being packed with an adsorbent exhibiting a selective adsorbability for a specified component in a feed solution containing two or more components.

BACKGROUND ART OF THE INVENTION

It is well known that, in a simulated moving-bed type chromatographic separator, a plurality of unit packed columns (hereinafter, also referred to as simply "packed column"), each packed with an adsorbent exhibiting a selective adsorbability for a specified component among two or more components contained in a feed solution, are connected in series, and an endless circulation system is formed by connecting a most downstream-side unit packed column to a most upstream-side unit packed column to form a packed bed as a whole, and the feed solution and eluent are supplied to the packed bed, a fraction (fraction A) high in moving speed in the packed bed and a fraction (fraction C) low in moving speed in the packed bed are extracted, respectively, from positions different from each other, and the position for supply of the feed solution, the position for supply of the eluent, the position for extraction of the fraction A and the position for extraction of the fraction C are moved in order toward the downstream side in the fluid circulation direction in the packed bed while being maintained at a constant positional relationship, thereby simulatively realizing an operation of a moving bed capable of performing a continuous supply of feed solution (for example, Patent document 1).

In such a simulated moving-bed type chromatographic separator, because the liquid is circulated in the packed bed while the supply of the feed solution and the eluent and the extraction of fractions A and C are always carried out, usually, at least a feed solution supply pump, an eluent supply pump and one or more circulation pump are required. In particular, because the circulation pump is fixed between certain unit packed columns, the discharge amount thereof varies periodically accompanied with the supply of the feed solution, the supply of the eluent or the extraction of the respective fractions. Further, because the concentration and the composition of the fluid flowing into the circulation pump vary in order, accompanying therewith, the properties such as specific gravity and viscosity of the fluid vary. As a difference between the set value of the flow rate of the circulation pump and the actual flow rate of the actual fluid becomes greater, the separation ability decreases. Therefore, an expensive control device is required in order to automatically control the flow rate of the circulation pump in accordance with such an alteration of the flow rate set value or a variation of the properties.

Further, as an operation method which is not a general simulated moving-bed type chromatographic separation wherein a liquid is circulated in a packed bed while supply of feed solution and eluent and extraction of fractions A and C are always carried out, many operation methods are proposed, such as those disclosed in Patent documents 2 and 3. In an operation method disclosed in Patent document 2, although the control is simple and a high separation performance can be obtained, because the concentration and the composition of the fluid flowing into the circulation pump also vary, accompanying therewith the properties such as specific gravity and viscosity of the fluid also vary. Further, since the circulation pump is periodically repeated in operation/stop, the pressure variation in the system becomes great, and in order to avoid this, an operation such as delaying the timing of shutting off the inside of the packed bed becomes necessary, and whereby, the control becomes complicated.

Patent document 1: Japanese Patent 2,962,589
Patent document 2: JP-A-2001-334103
Patent document 3: JP-B-60-55162

DISCLOSURE OF THE INVENTION

Problems to be Solved by the Invention

An object of the present invention is to provide an inexpensive simulated moving-bed type chromatographic separator capable of obtaining a high separation ability by a small and simple structure. In particular, an object of the present invention is to provide a simpler simulated moving-bed type chromatographic separator by making an eluent supply pump or/and a feed solution supply pump perform the role of a circulation pump in a conventional separator.

Means for Solving the Problems

To achieve the above-described objects, a chromatographic separator according to the present invention comprises a circulation system, in which a plurality of unit packed columns, each packed with an adsorbent exhibiting a selective adsorbability for a specified component in a feed solution containing two or more components, are provided, the plurality of unit packed columns are connected in series by pipes and a most downstream-side unit packed column is connected to a most upstream-side unit packed column to form an endless circulation system forming a packed bed as a whole, and adsorption zones separated in order with respect to affinity relative to adsorbent are formed by feeding the feed solution containing two or more components to the packed bed, and the chromatographic separator performs chromatographic separation by combining a first process for supplying at least one of the feed solution and eluent into the circulation system and extracting the same quantity as that of liquid supplied into the circulation system from a position in the circulation system corresponding to a packed column where some component is enriched, and a second process for circulating liquid in the circulation system without supplying the feed solution and the eluent and extracting a separated component at all. The chromatographic separator is characterized in that, in the first process, the feed solution and the eluent are supplied into the circulation system using a feed solution supply pump and an eluent supply pump, respectively, and the total quantity of liquid to be extracted is extracted from one position in the circulation system by the same quantity as that of liquid supplied into the circulation system, and in the second process, the total quantity of liquid to be extracted is extracted from at least one position in the circulation system, liquid extracted from the circulation system is flowed into the eluent supply pump or/and the feed solution supply pump and the liquid extracted from the circulation system is supplied again into the circulation system using the eluent supply pump or/and the feed solution supply pump so as to carry out circulation of the circulation system.

In such a chromatographic separator, in a case where the eluent supply pump is used in the second process, it is preferred to extract the liquid from a position lowest in concentration in the circulation system. Further, in a case where the feed solution supply pump is used, it is preferred to extract the liquid from a position highest in concentration in the circulation system. By employing such a manner, it becomes possible to move the adsorption zones in the circulation system without disturbing the adsorption zones. Further, since the liquid flowing into the eluent supply pump and the feed solution supply pump is little in concentration change, that is, little in viscosity change, they can discharge liquid at a set flow rate without providing a particular flow rate control means.

Further, in the second process, in a case where one of the eluent supply pump and the feed solution supply pump is used, the pressure loss in the circulation system must be covered by the one pump, and it is necessary to set the specification of pressure for the circulation system at a high value. However, in a case where the eluent supply pump and the feed solution supply pump are both used, because the pressure loss in the circulation system is covered by the two pumps, it becomes possible to reduce the specification of pressure for the circulation system. Namely, in the present invention, a structure may be employed wherein, in the second process, the total quantity of liquid to be extracted is extracted from two positions in the circulation system, the liquid extracted from the circulation system is flowed into the eluent supply pump and the feed solution supply pump, respectively, and the liquid extracted from the circulation system is supplied again into the circulation system using these eluent supply pump and feed solution supply pump so as to carry out circulation of the circulation system.

Further, in a case where the feed solution supply pump is not used in the second process, a structure may be employed wherein feed solution in pipes is always circulated by utilizing a feed solution return pipe, without stopping the feed solution supply pump.

Further, in the chromatographic separator according to the present invention, it is preferred that, in the first process, a position for supplying the feed solution or the eluent and a position for extracting each component are moved in order toward a downstream side of the circulation system in accordance with a movement of the adsorption zones in the circulation system.

As to extraction of each fraction, for example, a structure may be employed wherein, in the first process, with respect to a first fraction containing much non-adsorptive substance low in adsorbability relative to adsorbent and a second fraction containing much adsorptive substance high in adsorbability relative to adsorbent, any of at least extraction of the first fraction by supply of the feed solution, extraction of the first fraction by supply of the eluent, extraction of the second fraction by supply of the feed solution, and extraction of the second fraction by supply of the eluent, are combined and carried out.

In addition to such an extraction, in the first process, any of at least extraction of the first fraction by supply of the feed solution and the eluent, and extraction of the second fraction by supply of the feed solution and the eluent, may be further combined and carried out.

Further, in the chromatographic separator according to the present invention, a structure may be employed wherein a flow speed is gradually increased during a period from a time immediately after supply of the feed solution to a time immediately before next supply of the feed solution. In the separator according to the present invention, because the supply of the feed solution is carried out intermittently, in the concentration distribution in the circulation system, the concentration is highest at the time immediately after the supply of the feed solution and lowest at the time immediately before the supply of the feed solution. Therefore, a pressure loss is most liable to occur at the time immediately after the supply of the feed solution, and a pressure loss is most hardly liable to occur at the time immediately before the supply of the feed solution. Accordingly, by gradually increasing the flow speed from the time immediately after the supply of the feed solution, the specification of pressure of the circulation system can be utilized effectively for improving the efficiency of the separation. Further, the time required for one cycle can be shortened, and the production amount per adsorbent amount can be increased.

Effect According to the Invention

In the chromatographic separator according to the present invention, the first and second processes can be carried out by two pumps of the feed solution supply pump and the eluent supply pump, and while the separator is easy in pump control and simple and inexpensive as a whole, a high, stable separation performance can be obtained.

In particular, because the extraction port may be a single port, a complicated control means is not required, and an inexpensive separator can be provided.

Further, since it becomes possible to smoothly extract respective components by usual valves even if back pressure regulating valves and the like are not used on extraction lines, the specification of pressure for the circulation system can be reduced.

Furthermore, as compared with a case where a pump is installed in a circulation system, the variation of the properties such as concentration or viscosity of the liquid flowing into a pump can be decreased, the pump can exhibit its set flow rate easily, and a stable separation performance can be obtained.

BRIEF EXPLANATION OF THE DRAWINGS

[FIG. 1]

[FIG. 2]

[FIG. 3]

EXPLANATION OF SYMBOLS 1, 31, 41: chromatographic separator
2: feed solution tank
3: feed solution
4: unit packed column
5: adsorbent
6: pipe
7: circulation system
8: fraction A extracting line
9: fraction A joining pipe
10: fraction C extracting line
11: fraction C joining pipe
12: circulated liquid extracting line (in a case using an eluent supply pump)

13: circulated and extracted liquid joining pipe (in a case using an eluent supply pump)
14: check valve
15: eluent tank
16: eluent
17: feed solution supplying line
18: divergent feed solution supplying line
19: feed solution circulating line
20: eluent supplying line
21: divergent eluent supplying line
22: circulated liquid extracting line (in a case using a feed solution supply pump)
23: circulated and extracted liquid joining pipe (in a case using a feed solution supply pump)
24: fraction B extracting line (in a case carrying out multi-component separation)
PD: eluent supply pump
PF: feed solution supply pump
A1, A2, A3, A4: fraction A extracting valve
B4: fraction B extracting valve
C1, C2, C3, C4: fraction C extracting valve
D1, D2, D3, D4: eluent supplying valve
F1, F2, F3, F4: feed solution supplying valve
R1, R2, R3, R4: shutoff valve
Y1, Y2, Y3, Y4: total quantity extracting valve (in a case using a feed solution supply pump)
Z1, Z2, Z3, Z4: total quantity extracting valve (in a case using an eluent supply pump)

THE BEST MODE FOR CARRYING OUT THE INVENTION

Hereinafter, desirable embodiments of the chromatographic separator according to the present invention will be explained referring to figures.

Figure 1:
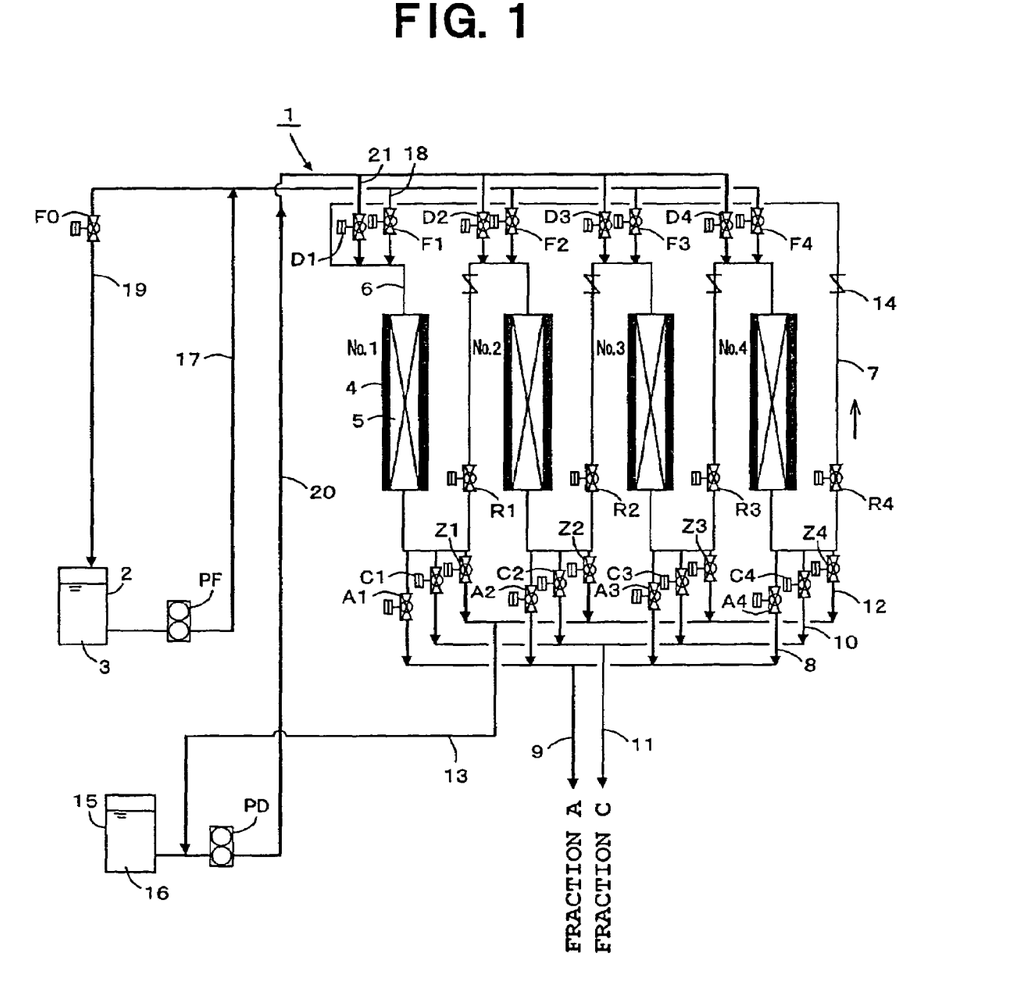
FIG. 1 is a system diagram of a chromatographic separator according to an embodiment (separation of two components) of the present invention.

FIG. 1 shows a chromatographic separator according to an embodiment of the present invention, and in particular, shows an example of a chromatographic separator wherein, in the second process in the present invention, the total quantity of liquid to be extracted is extracted from one position in a circulation system, and the adsorption zones in the circulation system are moved using an eluent supply pump. Chromatographic separator 1 has four unit packed columns 4 (No. 1 to No. 4 packed columns), and in each packed column 4, an adsorbent 5, which exhibits a selective adsorbability for a specified component in a feed solution 3 containing two or more components and supplied from a feed solution tank 2, is packed. The exit of each packed column 4 is connected to the entrance of an adjacent packed column 4, respective packed columns 4 are connected in series as a whole by pipes 6, and all the packed columns 4 are connected in an endless form by connecting the exit of a most downstream-side unit packed column 4 (for example, No. 4 packed column 4 in FIG. 1) to the entrance of a most upstream-side unit packed column 4 (for example, No. 1 packed column 4 in FIG. 1) by pipe 6. Therefore, this packed bed formed by connecting all unit packed columns 4 at an endless form is formed as a circulation system 7 in which a fluid can be circulated in the arrow direction.

Shutoff valves R1, R2, R3 and R4 and check valves capable of shutting off between respective packed columns are provided between respective adjacent packed columns 4 in circulation system 7. Fraction A extracting valves A1, A2, A3 and A4 are provided between respective shutoff valves R1, R2, R3 and R4 and the exits of respective packed columns 4 positioned at upstream sides thereof, for the purpose of extracting a fraction having a high moving speed in the packed bed (fraction A: a first fraction containing much non-adsorptive substance low in adsorbability relative to adsorbent). Respective fraction A extracting lines 8 are joined into a single fraction A joining pipe 9. Similarly, fraction C extracting valves C1, C2, C3 and C4 are provided for the purpose of extracting a fraction having a low moving speed in the packed bed (fraction C: a second fraction containing much a dsorptive substance high in adsorbability relative to adsorbent). Respective fraction C extracting lines 10 are joined into a single fraction C joining pipe 11. Except these, two-way valves Z1, Z2, Z3 and Z4 are provided for the purpose of extracting the total quantity of liquid to be extracted in the circulation process. Respective circulated liquid extracting lines 12 are joined into a circulated and extracted liquid joining pipe 13, and it is joined to an eluent supplying line 20 at a position upstream eluent supply pump PD.

To circulation system 7, feed solution 3 and eluent 16 stirred in eluent tank 15 can be supplied. In this embodiment, feed solution 3 is supplied by feed solution supply pump PF capable of controlling the flow rate of the supplied feed solution via feed solution supplying line 17. Feed solution supplying line 17 is diverged into respective divergent feed solution supplying lines 18, and feed solution can be supplied to the entrance sides of the respective unit packed columns 4 via respective divergent feed solution supplying lines 18. Feed solution supplying valves F1, F2, F3 and F4 capable of being opened/closed are provided respective divergent feed solution supplying lines 18, and the feed solution is supplied through a line with an opened valve to a corresponding unit packed column. Where, in a case where the feed solution supply pump PF is required to be operated even in a process in which the feed solution is not supplied for the purpose of safe operation of the feed solution supply pump PF, a structure may be employed wherein a valve F0 and a feed solution circulating line 19 are provided at a position upstream the feed solution supply pump PF and the feed solution is returned to feed solution tank 2.

In this embodiment, the circulated fluid is extracted at its total quantity through any one of valves Z1 to Z4, the extracted fluid is joined to the upstream side of eluent supply pump PD, which is positioned between eluent tank 15 and eluent supply pump PD, through circulated and extracted liquid joining pipe 13, and the fluid is supplied again to circulation system 7 through eluent supplying line 20 by eluent supply pump PD capable of controlling the flow rate of the supplied fluid. Eluent supplying line 20 is diverged into respective divergent eluent supplying lines 21, and the eluent can be supplied to the entrance sides of respective unit packed columns 4 through respective divergent eluent supplying lines 21. Eluent supplying valves D1, D2, D3 and D4 capable of being opened/closed are provided to respective divergent eluent supplying lines 21, and the eluent is supplied through an opened eluent supplying valve to a corresponding unit packed column 4. Where, in a case where the eluent supply pump PD is required to be operated even in a process other than a process of supplying eluent and a circulation process for the purpose of safe operation of the eluent supply pump PD, a structure may be employed wherein an eluent circulating line is provided at a position upstream the eluent supply pump and the eluent is returned to eluent tank 15.

In such a chromatographic separator 1, separation is carried out as follows.

Namely, in chromatographic separator 1, it is possible to operate four processes of a process wherein the feed solution is supplied and the total quantity of the fluid is extracted from fraction A extracting position, a process wherein the eluent is supplied and the total quantity of the fluid is extracted from fraction C extracting position, a process wherein the eluent is supplied and the total quantity of the fluid is extracted from fraction A extracting position, and a process wherein supply, extraction and shutoff are not carried out at all and the liquid in the circulation system is circulated, and the separation can be carried out by combining these processes.

In the process wherein the feed solution is supplied and the total quantity of the fluid is extracted from fraction A extracting position (process F-A), any feed solution supplying valve is opened, the feed solution is supplied into circulation system 7 from the entrance side of a corresponding unit packed column 4, fraction A extracting valve A corresponding the fraction A extracting position (any of valves A1 to A4) is opened, a shutoff valve R present at a position immediately downstream thereof (any of valves R1 to R4) is closed, and the total quantity of fraction A is extracted through fraction A extracting line 8.

In the process wherein the eluent is supplied and the total quantity of the fluid is extracted from fraction C extracting position (process D-C), any eluent supplying valve is opened, the eluent is supplied into circulation system 7 from the entrance side of a corresponding unit packed column 4, fraction C extracting valve C corresponding the fraction C extracting position (any of valves C1 to C4) is opened, a shutoff valve R present at a position immediately downstream thereof (any of valves R1 to R4) is closed, and the total quantity of fraction C is extracted through fraction C extracting line 10.

In the process wherein the eluent is supplied and the total quantity of the fluid is extracted from fraction A extracting position (process D-A), any eluent supplying valve is opened, the eluent is supplied into circulation system 7 from the entrance side of a corresponding unit packed column 4, fraction A extracting valve A corresponding the fraction A extracting position (any of valves A1 to A4) is opened, a shutoff valve R present at a position immediately downstream thereof (any of valves R1 to R4) is closed, and the total quantity of fraction A is extracted through fraction A extracting line 8.

In the process wherein supply, extraction and shutoff are not carried out at all and the liquid in the circulation system is moved (circulation process), any circulated fluid extraction valve (any of valves Z1 to Z4) is opened, a shutoff valve R present at a position immediately downstream thereof (any of valves R1 to R4) is closed, the total quantity of the fluid is extracted from circulated liquid extracting line 12 to outside of the circulation system 7, and the extracted fluid is supplied from eluent supplying valve D corresponding to the eluent supplying position (any of valves D1 to D4) via eluent supply pump PD.

Next, the opening/closing cycles of the respective valves will be explained. An example of this operation is shown in Table 1. In Table 1, control conditions of opening/closing of valves F and D are shown, the numerals in the Table indicate the numbers of the respective valves (for example, "1" in the item of valve F indicates a valve F1), and a condition is indicated that the valve having the number is opened. A blank column indicates a condition being closed. Further, in the items of valves A and C and circulated fluid extracting valve Z, the number of a valve performing extraction of the total quantity is shown. A blank column indicates a condition where the extraction by the valve is not carried out. As to valve R, a condition is shown where the valve described with the number is closed. A blank column indicates a condition where the valve is opened. Moreover, as to the items of feed solution supply pump PF and eluent supply pump PD, the circular mark indicates an operation condition, and the blank indicates a stopped condition. In this Table 1, the cycle from process No. 1-1 to 1-4 to process No. 4-1 to 4-4 shows one cycle of separation in the present chromatographic separator 1.

TABLE 1

| Process | Opening/closing of valve | | | | | | Pump | |
|---|---|---|---|---|---|---|---|---|
| No. | F | D | A | C | Z | R | PF | PD |
| 1-1 | 1 | | 1 | | | | ○ | |
| 1-2 | 0 | 3 | | 3 | | | ○ | ○ |
| 1-3 | 0 | 3 | 1 | | | | ○ | ○ |
| 1-4 | 0 | 3 | | | 2 | 2 | ○ | ○ |
| 2-1 | 2 | | 2 | | | | ○ | |
| 2-2 | 0 | 4 | | 4 | | | ○ | ○ |
| 2-3 | 0 | 4 | 2 | | | | ○ | ○ |
| 2-4 | 0 | 4 | | | 3 | 3 | ○ | ○ |
| 3-1 | 3 | | 3 | | | | ○ | |
| 3-2 | 0 | 1 | | 1 | | | ○ | ○ |
| 3-3 | 0 | 1 | 3 | | | | ○ | ○ |
| 3-4 | 0 | 1 | | | 4 | 4 | ○ | ○ |
| 4-1 | 4 | | 4 | | | | ○ | |
| 4-2 | 0 | 2 | | 2 | | | ○ | ○ |
| 4-3 | 0 | 2 | 4 | | | | ○ | ○ |
| 4-4 | 0 | 2 | | | 1 | 1 | ○ | ○ |

(As to Process 1-1)

With processes No. 1-1 to 1-4, in process 1-1, feed solution supplying valve F1 is opened and the feed solution is supplied into circulation system 7, fraction A extracting valve A1 is opened, and therefrom, the total quantity of fraction A is extracted. Therefore, this process 1-1 corresponds to a process according to the present invention wherein the feed solution is supplied and the total quantity is extracted from fraction A extracting position.

(As to Process 1-2)

In process 1-2, eluent supplying valve D3 is opened and the eluent is supplied into circulation system 7, fraction C extracting valve C3 is opened, and therefrom, the total quantity of fraction C is extracted. Therefore, this process 1-2 corresponds to a process according to the present invention wherein the eluent is supplied and the total quantity is extracted from fraction C extracting position.

(As to Process 1-3)

In process 1-3, eluent supplying valve D3 is opened and the eluent is supplied into circulation system 7, fraction A extracting valve A1 is opened, and therefrom, the total quantity of fraction A is extracted. Therefore, this process 1-3 corresponds to a process according to the present invention wherein the eluent is supplied and the total quantity is extracted from fraction A extracting position. At that time, the feed solution is returned to feed solution tank 2 through valve F0.

(As to Process 1-4)

In process 1-4, circulated fluid extracting valve Z2 is opened, and therefrom, the total quantity of the circulated fluid is extracted from circulation system 7. The extracted circulated fluid is supplied again into the circulation system 7 by eluent supply pump PD from eluent supplying valve D3. Therefore, this process 1-4 corresponds to a process according to the present invention (the second process) wherein supply, extraction and shutoff are not carried out at all, and the liquid in the circulation system is moved and circulated relatively to the circulation system. At that time, the feed solution is returned to feed solution tank 2 through valve F0.

Such processes 1-1 to 1-4 in series due to valve switching are carried out at a condition where supplying positions of feed solution and eluent, extracting positions of fractions A and C and circulated fluid extracting valve position in the circulation process are maintained at a specified positional relationship. After these processes 1-1 to 1-4 in series finish, while the specified positional relationship is maintained, the position of each valve to be controlled is shifted to a downstream side by one valve position, and the following processes 2-1 to 2-4 in series are carried out. By carrying out this shit in order, a function equal to the operation of a known simulated moving-bed type chromatographic separator can be achieved.

In the processes 2-1 to 2-4, processes 3-1 to 3-4 and processes 4-1 to 4-4 following the processes 1-1 to 1-4, at a condition where the position of each valve is shifted by one valve position as described above, the operations similar to that in the above-described processes 1-1 to 1-4 are carried out. When the operation from the process 1-1 to the process 4-4 is completed, one cycle of the separation finishes.

In the above-described operation for separation, feed solution supply pump PF and eluent supply pump PD may be set a constant flow rate, or may be controlled with flow rate.

Thus, in chromatographic separator 1 according to the present invention, the operation can be achieved by two pumps. In the circulation process, the circulated fluid immediately before supply of eluent in circulation system 7 is extracted from circulated fluid extracting valve Z by the total quantity, and utilizing eluent supply pump PD, the extracted fluid is supplied from the eluent supplying valve D positioned immediately downstream of the valve Z served to the extraction. Namely, by making the eluent supply pump PD commonable for the process for supplying eluent and the process for carrying out circulation in circulation system 7, the total number of pumps required for the operation of separation can be reduced down to two, and the structure of chromatographic separator as a whole can be greatly simplified.

Further, because the circulated fluid extracted in the circulation process is lowest in concentration of feed solution and closest to eluent in properties such as specific gravity and viscosity in circulation system 7, the properties such as specific gravity and viscosity of the eluent and the circulated fluid flowing into eluent supply pump PD are always stable during the operation of separation. By this, without a control device in the circulation process, or, with only a simple and inexpensive control device, it becomes possible to operate at a stable flow rate close to a set value by a conventional method, and the separation performance can be stabilized.

Further, because respective components can be extracted by usual valves unless a back pressure regulating valve is used in the extraction side, the specification of pressure in the circulation system can be reduced, and from this point of view, simplification and cost down of chromatographic separator 1 become possible.

Figure 2:
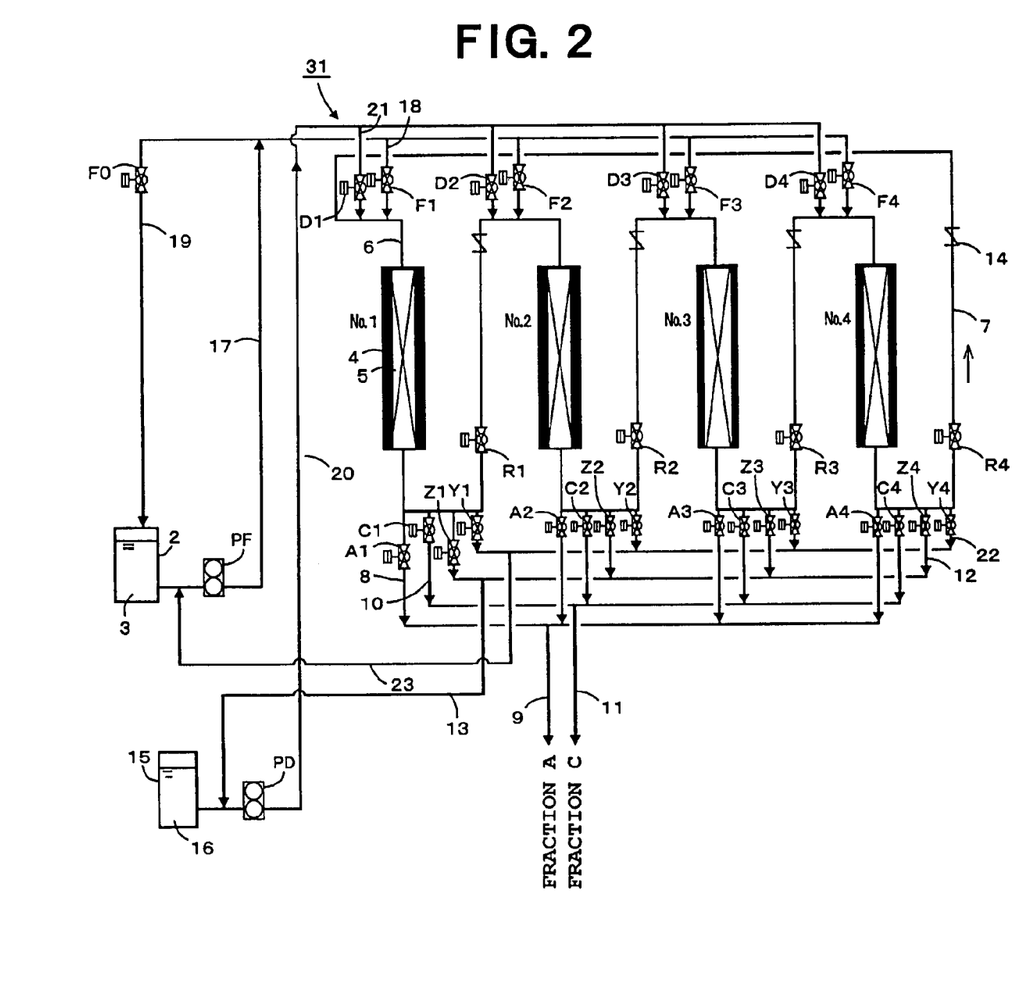
FIG. 2 is a system diagram of a chromatographic separator according to another embodiment (separation of two components) of the present invention.

FIG. 2 shows a chromatographic separator according to another embodiment of the present invention, and shows an example of a chromatographic separator wherein the total quantity is extracted from two positions in a circulation system in the second process of the present invention, and the adsorption zones in the circulation system are moved using both of an eluent supply pump and a feed solution supply pump.

In a chromatographic separator 31 shown in FIG. 2, two-way valves Z1, Z2, Z3 and Z4 and Y1, Y2, Y3 and Y4 are provided for the purpose of extracting the total quantity of liquid to be extracted in the circulation process. Respective circulated liquid extracting lines 12 from the valves Z1, Z2, Z3 and Z4 are joined into a circulated and extracted liquid joining pipe 13, and it is joined to an eluent supplying line 20 at a position upstream eluent supply pump PD. Respective circulated liquid extracting lines 22 from the valves Y1, Y2, Y3 and Y4 are joined into a circulated and extracted liquid joining pipe 23, and it is joined to a feed solution supplying line 17 at a position upstream feed solution supply pump PF.

Z line and D line, and Y line and F line, will be explained. In this embodiment, the circulated fluid is extracted at any of valves Z1, Z2, Z3 and Z4 by the total quantity, the fluid is joined to an upstream position of eluent supply pump PD between eluent tank 15 and the eluent supply pump PD, and the fluid is supplied again into circulation system 7 through eluent supplying line 20 by the eluent supply pump PD capable of controlling the flow rate of the supplied fluid, and at the same time, the circulated fluid is extracted at any of valves Y1, Y2, Y3 and Y4 by the total quantity, the fluid is joined to an upstream position of feed solution supply pump PF between feed solution tank 2 and the feed solution supply pump PF, and the fluid is supplied again into the circulation system 7 through feed solution supplying line 17 by the feed solution supply pump PF capable of controlling the flow rate of the supplied fluid.

Thus, by supplying the circulated fluid extracted from circulation system 7 again into the circulation system 7 using both of eluent supply pump PD and feed solution supply pump PF, as aforementioned, because the pressure loss in the circulation system 7 is covered by the two pumps, it becomes possible to reduce the specification of pressure for the circulation system 7. Other operations and advantages are similar to those in the embodiment shown in FIG. 1.

Figure 3:
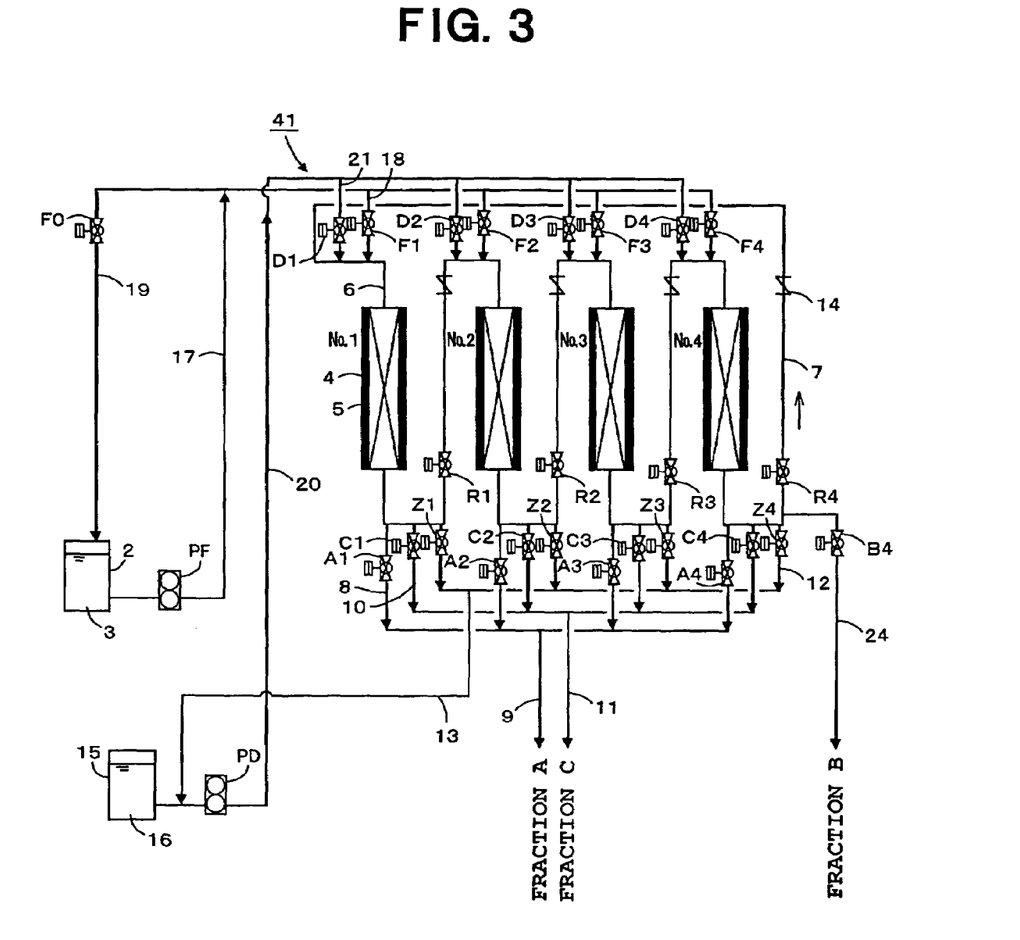
FIG. 3 is a system diagram of a chromatographic separator according to a further embodiment (separation of three components) of the present invention.

FIG. 3 shows a chromatographic separator 41 according to a further embodiment of the present invention, and in particular, shows an example of a chromatographic separator for a case where a multi-component separation is carried out in the present invention (in this embodiment, an example of separation of three components). Although the adsorption zones in circulation system 7 are moved using eluent supply pump PD, by adding lines and valves corresponding to the Y lines and the valves Y shown in FIG. 2, it becomes possible to carry out both of the case where feed solution supply pump PF is used and the case where both of the eluent supply pump PD and the feed solution supply pump PF are used.

In this embodiment, as compared with the embodiments shown in FIGS. 1 and 2 where fraction A and fraction C are extracted, fraction B is further extracted. In this case, a fraction B extracting valve B4 is provided for the purpose of extracting a fraction having an intermediate moving speed (fraction B) relative to a fraction having a high moving speed in the circulation system and a fraction having a low moving speed. The fraction B is extracted from fraction B extracting line 24 to the outside of circulation system 7.

As to the opening/closing cycles of the respective valves, an example of the operation is shown in Table 2. In Table 2, the cycle from process No. 1-1 to 1-4 to process No. 4-1 to 4-3 shows one cycle of separation in the present chromatographic separator 41.

TABLE 2

| Process | Opening/closing of valve | | | | | | | Pump | |
|---------|---|---|---|---|---|---|---|------|------|
| No. | F | D | A | B | C | Z | R | PF | PD |
| 1-1 | 1 | 3 |   | 4 |   |   |   | ○ |   |
| 1-2 | 0 | 3 | 1 |   |   |   |   | ○ | ○ |
| 1-3 | 0 | 3 |   |   | 3 |   |   | ○ | ○ |
| 1-4 | 0 | 3 |   |   |   | 2 | 2 | ○ | ○ |
| 2-1 | 0 | 4 | 2 |   |   |   |   | ○ | ○ |
| 2-2 | 0 | 4 |   |   | 4 |   |   | ○ | ○ |
| 2-3 | 0 | 4 |   |   |   | 3 | 3 | ○ | ○ |
| 3-1 | 0 | 1 | 3 |   |   |   |   | ○ | ○ |

TABLE 2-continued

| Process | Opening/closing of valve | | | | | | | Pump | |
|---|---|---|---|---|---|---|---|---|---|
| No. | F | D | A | B | C | Z | R | PF | PD |
| 3-2 | 0 | 1 | | | 1 | | | ○ | ○ |
| 3-3 | 0 | 1 | | | | 4 | 4 | ○ | ○ |
| 4-1 | 0 | 2 | 4 | | | | | ○ | ○ |
| 4-2 | 0 | 2 | | | 2 | | | ○ | ○ |
| 4-3 | 0 | 2 | | | | 1 | 1 | ○ | ○ |

In this embodiment, fraction B is extracted in the process 1-1 (process FD–B). Namely, feed solution is supplied into circulation system 7 from the entrance side of a corresponding unit packed column 4, eluent is supplied into the circulation system 7 from the entrance side of a corresponding unit packed column 4, the total quantity of fraction B equal to the sum of the supplied feed solution and eluent is extracted through fraction B extracting line 24 by opening fraction B extracting valve B at a position corresponding to a fraction B extracting position and closing a shutoff valve present at a position of immediately downstream side thereof. The extraction of fractions A and C is performed similarly to in the aforementioned embodiments.

Although an example of three component extraction is shown in FIG. 3, in a case where four or more component extraction is carried out, it becomes possible to perform such multi-component separation by diverging the fraction B extracting line and collecting respective fractions with respective enriched components separately.

EXAMPLES

Example 1

Using chromatographic separator 1 shown in FIG. 1, a feed solution with a total sugar concentration of 60%, which comprised 52% of glucose, 42% of fructose and 6% of disaccharide, was separated by the simulated moving-bed type chromatographic separator using water as eluent. In the separator shown in FIG. 1, each unit packed column 4 was made as a cylindrical unit packed column having an inner diameter of 20 mm and a height of 0.9 m, and 1.13 L of strong acid-type cation exchange resin of calcium type "Amberlite" CR1220 (produced by Rohm and Haas Corporation) was charged into each packed column 4. The inside of each unit packed column 4 was kept at about 60° C. In this simulated moving bed, the operation was performed based on the operation process shown in Table 1 at the following conditions of amounts to be supplied of feed solution and water (amounts to be supplied per one cycle) shown in Table 3.

The sugar composition of glucose group liquid (non-adsorptive fraction: first fraction) and fructose fraction group liquid (adsorptive fraction: second fraction) extracted at a stationary state is shown in Table 4. Further, the recovery percentages thereof are shown in Table 5.

TABLE 3

| | |
|---|---|
| Supply amount of feed solution | 0.023 L |
| Supply amount of water | 0.230 L |
| Glucose group liquid extracted amount | 0.135 L |
| Fructose group liquid extracted amount | 0.118 L |
| Circulation amount | 0.760 L |
| Time for one cycle | 0.44 H |

TABLE 4

| | Non-adsorptive fraction | Adsorptive fraction |
|---|---|---|
| Concentration | 7.1% | 5.9% |
| Disaccharide | 8.9% | 1.5% |
| Glucose | 86.1% | 0.9% |
| Fructose | 5.0% | 97.6% |

TABLE 5

| | Non-adsorptive fraction | Adsorptive fraction |
|---|---|---|
| Disaccharide | 87.7% | 12.3% |
| Glucose | 99.2% | 0.8% |
| Fructose | 7.0% | 93.0% |

As is evident from Tables 4 and 5, while the number of the unit packed columns was few to be four columns and a simple structure of two pumps was employed, a high separation efficiency and a high recovery percentage could be achieved.

Example 2

Using chromatographic separator 41 shown in FIG. 3, a feed solution with a total sugar concentration of 60%, which comprised 48% of glucose, 49.5% of maltose and 2.5% of tri- or more saccharide, was separated by the simulated moving-bed type chromatographic separator using water as eluent. In the separator shown in FIG. 3, each unit packed column 4 was made as a cylindrical unit packed column having an inner diameter of 20 mm and a height of 1.8 m, and 2.26 L of strong acid-type cation exchange resin of calcium type "Amberlite" CR1220 (produced by Rohm and Haas Corporation) was charged into each packed column 4. The inside of each unit packed column 4 was kept at about 60° C. In this simulated moving bed, the operation was performed based on the operation process shown in Table 2 at the following conditions of amounts to be supplied of feed solution and water (amounts to be supplied per one cycle) shown in Table 6.

The sugar composition of tri- or more saccharide fraction liquid, maltose fraction liquid and glucose fraction liquid extracted in a stationary state is shown in Table 7. Further, the recovery percentages thereof are shown in Table 8.

TABLE 6

| | |
|---|---|
| Supply amount of feed solution | 0.070 L |
| Supply amount of water | 0.692 L |
| Tri-or more saccharide group liquid extracted amount | 0.262 L |
| Maltose group liquid extracted amount | 0.211 L |
| Glucose group liquid extracted amount | 0.290 L |
| Circulation amount | 1.076 L |
| Time for one cycle | 1.15 H |

TABLE 7

| | Tri-or more saccharide fraction | Maltose fraction | Glucose fraction |
|---|---|---|---|
| Concentration | 0.5% | 12.1% | 9.1% |
| Tri-or more saccharide | 66.0% | 1.5% | 0.3% |
| Maltose | 13.5% | 94.5% | 7.5% |
| Glucose | 20.5% | 4.0% | 92.2% |

TABLE 8

|  | Tri-or more saccharide fraction | Maltose fraction | Glucose fraction |
|---|---|---|---|
| Tri-or more saccharide | 64.2% | 29.7% | 6.1% |
| Maltose | 0.7% | 91.8% | 7.5% |
| Glucose | 1.0% | 4.0% | 95.0% |

As is evident from Tables 7 and 8, while the number of the unit packed columns was few to be four columns and a simple structure of two pumps was employed, a high separation efficiency and a high recovery percentage for all of three components could be achieved.

Thus, in the simulated moving bed-type chromatographic separator according to the present invention, the number of unit packed columns is few, the separator can be operated by only two pumps of a feed solution supply pump and an eluent supply pump, and while the separator is easy-to-control, simple as a whole and inexpensive, a high and stable separation performance can be achieved.

INDUSTRIAL APPLICATIONS OF THE INVENTION

The chromatographic separator according to the present invention can be applied to any separation of feed solution required to be separated into two components or three or more components, and in particular, as shown in the examples, it is suitable for the separation of sugar components.

The invention claimed is:

1. A chromatographic separator to be operated in a circulation system, said chromatographic separator comprising a plurality of unit packed columns, each of said unit packed columns being packed with an adsorbent exhibiting a selective adsorbability for a specified component in a feed solution containing at least two components, said plurality of unit packed columns are connected in series by pipes and a most downstream-side unit packed column is connected to a most upstream-side unit packed column to form an endless circulation system forming a packed bed as a whole, and adsorption zones are separated in order with respect to affinity relative to an adsorbent, said chromatographic separator further comprises a feed solution supply pump and an eluent supply pump for respectively supplying said feed solution and said eluent into the circulation system, wherein said chromatographic separator is arranged such that the total quantity of liquid to be extracted is extracted from one position in said circulation system by the same quantity as that of liquid supplied into said circulation system, said chromatographic separator further comprises a plurality of valves, one of said plurality of valves being disposed between each of said unit packed columns and at least one of said eluent supply pump and said feed solution supply pump.

2. A chromatographic separator to be operated in a circulation system, said chromatographic separator comprising a plurality of unit packed columns, each of said unit packed columns being packed with an adsorbent exhibiting a selective adsorbability for a specified component in a feed solution containing at least two components, said plurality of unit packed columns are connected in series by pipes and a most downstream-side unit packed column is connected to a most upstream-side unit packed column to form an endless circulation system forming a packed bed as a whole, and adsorption zones are separated in order with respect to affinity relative to an adsorbent, said chromatographic separator further comprises a feed solution supply pump and an eluent supply pump for respectively supplying said feed solution and said eluent into the circulation system, wherein said chromatographic separator is arranged such that the total quantity of liquid to be extracted is extracted from one position in said circulation system by the same quantity as that of liquid supplied into said circulation system, said chromatographic separator further comprises a first plurality of valves, one of said first plurality of valves being disposed between each of said unit packed columns and said eluent supply pump and a second plurality of valves disposed between each of said unit packed columns and said feed solution supply pump.

* * * * *